United States Patent [19]

Schoenwald et al.

[11] Patent Number: 5,179,124

[45] Date of Patent: Jan. 12, 1993

[54] ANTI-INFLAMMATORY FOR USE IN EXTERNAL AND INTERNAL EYE INFLAMMATIONS

[75] Inventors: Ronald D. Schoenwald; Charles F. Barfknecht, both of Iowa City, Iowa

[73] Assignee: University of Iowa Research Foundation, Iowa City, Iowa

[21] Appl. No.: 590,789

[22] Filed: Oct. 1, 1990

Related U.S. Application Data

[63] Continuation-in-part of Ser. No. 147,974, Jan. 25, 1988, Pat. No. 4,968,718.

[51] Int. Cl.$^5$ .................. C07C 69/76; A01N 37/10
[52] U.S. Cl. .................. 514/532; 560/55; 562/465; 514/570
[58] Field of Search ............ 562/465; 560/55; 514/532, 570

[56] References Cited

U.S. PATENT DOCUMENTS

| | | | |
|---|---|---|---|
| 3,228,831 | 1/1966 | Nicholson | 167/53 |
| 3,991,206 | 11/1976 | Tolman et al. | 424/317 |
| 4,028,404 | 6/1977 | Bays et al. | 260/515 R |
| 4,181,736 | 1/1980 | Maillard | 424/317 |
| 4,251,543 | 2/1981 | Amano et al. | 424/317 |
| 4,599,360 | 7/1986 | Fukami et al. | 514/570 |
| 4,622,421 | 11/1986 | Terada et al. | 562/491 |

FOREIGN PATENT DOCUMENTS

| | | |
|---|---|---|
| 2250400 | 5/1973 | Fed. Rep. of Germany . |
| 2617592 | 11/1976 | Fed. Rep. of Germany . |
| 2814556 | 10/1978 | Fed. Rep. of Germany . |
| 2904799 | 8/1979 | Fed. Rep. of Germany . |
| 3026402 | 2/1982 | Fed. Rep. of Germany . |
| 2403325 | 5/1979 | France . |
| 52-53833 | 4/1977 | Japan . |
| 2027015 | 2/1980 | United Kingdom . |

*Primary Examiner*—Paul J. Killos
*Attorney, Agent, or Firm*—Zarley, McKee, Thomte, Voorhees & Sease

[57] ABSTRACT

An anti-inflammatory drug which is phenylacetic acid derivative and methods of using the same in topically controlling eye inflammations. The preferred drug is 2-[4(2-hydroxypropoxy)phenyl]propionic acid.

17 Claims, No Drawings

ANTI-INFLAMMATORY FOR USE IN EXTERNAL AND INTERNAL EYE INFLAMMATIONS

CROSS-REFERENCE TO A RELATED CASE

This application is a continuation-in-part of co-pending commonly assigned application Ser. No. 147,974, filed Jan. 25, 1988, now U.S. Pat. No. 4,968,718.

BACKGROUND OF THE INVENTION

This invention relates to a method and compositions useful in treating both internal and external eye inflammations. Specifically, this invention relates to methods and compositions which use certain nonsteroidal anti-inflammatory drugs to control internal and external eye inflammation.

For over a decade nonsteroidal anti-inflammatory drugs have been tested for their ability to suppress corneal inflammations. Indomethacin, fenoprofen, oxyphenbutazone, suprofen, and flurbiprofen were found to be effective in the laboratory and in the clinic for treating postoperative corneal inflammations. When compared to the commercially available topical corticosteroids, the nonsteroidal anti-inflammatory drugs are not as effective in treating corneal inflammations. Also, the currently available nonsteroidal anti-inflammatory drugs appear to have very little usefulness in clinically treating inflammations of the anterior chamber.

The nonsteroidal anti-inflammatory drugs were designed for systemic use and not for topical application to the eye. However, the requirements for optimal pharmacokinetics in the eye are quite different when compared to the systemic route of administration. An additional limitation to use of nonsteroids for ophthalmic use is their intrinsic pharmacological activity, which has been shown to be lower than the corticosteroids. These factors make it important to design molecules specially for the eye if topical application of nonsteroids is to be successful.

An object of this invention is to improve corneal penetration and most importantly, to improve distribution to and retention within, the iris/ciliary body tissue of nonsteroid drugs for inflammation treatment. Topical therapy using nonsteroidal anti-inflammatory drugs for corneal and anterior chamber inflammations would be very advantageous compared to the use of the corticosteroids. Steroids are responsible for various unwanted side effects, such as, an increase in intraocular pressure, delayed wound healing, cataract formation and corneal perforation.

As earlier stated, most inflammations of the eye are currently treated by other steroids which penetrate the eye and work effectively, but cause undesirable side effects. The undesirable side effects referred to earlier are exemplified by increased intraocular pressure, delayed wound healing, cataract formation and corneal perforations. On the other hand, if steroids are replaced with nonsteroidal anti-inflammatory drugs which do not penetrate the eye in therapeutic concentrations, they are generally effective only for external inflammations and thus have limited therapeutic application, i.e. pre-surgery. It thus can be seen that a continuing need exists for a drug which would both penetrate and be effective for not only external, but internal eye inflammations, and at the same time be free of systemic side effects.

The primary objective of the present invention is then to provide a nonsteroidal anti-inflammatory drug which will effectively penetrate the eye in therapeutic concentrations, which is effective for both internal and external inflammations, and which does not cause the typical systemic side effects of steroidal anti-inflammatory drugs.

Another objective of the present invention is to provide drugs which do not have one typical undesirable side effect of Ibuprofen, i.e. ulcer causation.

SUMMARY OF THE INVENTION

Certain phenylacetic acid derivatives have been found to be effective nonsteroidal anti-inflammation drugs for ophthalmic use. They are effective both for external inflammations and internal inflammations and do not cause systemic side effects, as do steroidal drugs. The invention discloses certain compounds of the type below described, and ophthalmically acceptable salt forms thereof, and the method of using the same for topically treating inflammations of the eye, and pharmaceutical compositions which contain these active anti-inflammatory nonsteroidal compounds.

DETAILED DESCRIPTION OF THE INVENTION

The compounds which are effective for use in this invention have the formula:

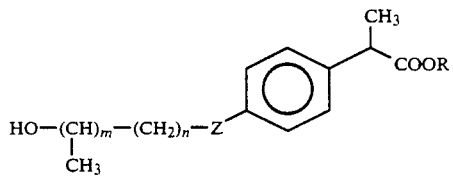

wherein R=H, $C_1$ to $C_6$ straight and branched chain alkyls with or without an additional hydroxyl, 6- or 1-[2-deoxy-a-D-arabino-hexopyranoside] or other 6- or 1-hexapyranoside/hexafuranosides, and N, N-di(2-hydroxyethyl)-2-hydroxyacetamide or other hydrophilic glycolamides; Z=oxygen or methylene; n=0 to 4; m=0 or 1. Included also are ophthalmically acceptable salt forms of each compound. These compounds may exist in several steroisomeric forms. All of the steroisomeric forms are therapeutically active. Thus, they are all intended to be within the scope of this invention, both (R, S) and racemic modifications thereof.

It is preferred that R=hydrogen and that Z=oxygen, and that m and n equal one. This compound has the formula:

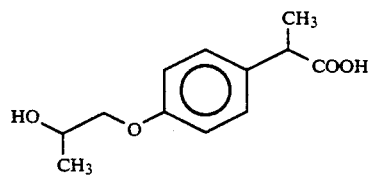

Its name is 2-[4-(2-hydroxypropoxy)phenyl]propionic acid.

It is believed that the active compound in most instances is where "R" equals hydrogen, but prodrugs may be metabolized to this form and be active. Thus, prodrugs which are designed to cross the cornea rapidly and metabolize to the active compound are included and may be desirable, such as the pivalyl.

The ophthalmically active compounds may be incorporated into various ophthalmic formulations for delivery to the eye. For example, the compounds may be combined with ophthalmologically acceptable preservatives, surfactants, viscosity enhancers, buffers, sodium chloride and water to form an aqueous ophthalmic solution or suspension. In order to form sterile ophthalmic ointment formulations, the active ingredient is combined with a preservative in an appropriate vehicle, such as mineral oil, liquid lanolin, or white petrolatum. Sterile ophthalmic gel formulations may be prepared by suspending the active nonsteroidal drugs of this invention in a hydrophilic base prepared from a combination of carbopol -940 (a carboxy vinyl polymer available from the B. F. Goodrich Company) according to published formulations for analogous ophthalmic preparations. Preservatives and tonicity agents can also be incorporated.

The specific type of formulation selected will depend on various factors, such as the type of ophthalmic inflammation being treated and dosage frequency. Ophthalmic solutions or suspensions suitable for easy eye drop administration, ointments nonaqueous solutions or suspensions and gels are the preferred dosage forms.

The active, nonsteroidal compounds of this invention will normally be contained in these formulations in an amount of from about 0.025% by weight to about 5.0% by weight, preferably from about 0.5% by weight to about 3.0% by weight. Thus, for topical presentation these formulations may be delivered in modest excess to the surface of the eye from 1-6 times per day depending upon the discretion of the clinician.

As heretofore mentioned, the compounds per se of the invention may be used or ophthalmically acceptable salt forms thereof. The ophthalmologically acceptable salts of the compounds of this invention include those formed from inorganic bases such as Group I hydroxides, like sodium hydroxide, and those formed from organic bases such as amines, etc.

Suitable ophthalmically acceptable carriers are generally known and of course must be non-eye-irritating, non-toxic, and allow for safe, easy eye administration topically. Generally for this invention aqueous-based systems wherein the carrier includes a buffer system to provide eye safe pH, a viscolyzer to provide suitable viscosity for eye comfort, an antibacterial agent, and a chemical preservative are adequate. The ophthalmically acceptable buffer should provide a composition having a pH within the range of about 5.5 to about 7.8, preferably from about 6.8 to about 7.4. Suitable ophthalmically acceptable buffers can be selected from the water soluble salt forms of citrate, borate, phosphate, carbonate, and acetate.

The viscolyzer suitable for use in this invention should provide the composition with a viscosity within the range of from about 4 centipoises to about 100 centipoises, preferably from about 5 centipoises to about 35 centipoises. Suitable viscolyzers can be selected from the group consisting of hydroxyethylcellulose, hydroxypropyl methylcellulose, methylcellulose and a polyacrylamide sold under the trade name GELAMIDE 250 by American Cyanamide.

In addition, the ophthalmic composition ideally will include antibacterials to provide safety and efficacy for storage stability. The amount of antibacterial can be within the range of from about 0.004% to about 0.5% by weight/volume of the composition. A suitable antibacterial would include, for example, from about 0.004% to about 0.02% by weight/volume of benzalkonium chloride, from about 0.25% to about 0.5% of chlorobutanol, about 0.1% of thimerosal, about 0.05% methylbaraben, about 0.01% propylbaraben, and sodium chloride in an amount sufficient to make an isotonic solution.

Finally, chemical preservatives may also be used, for example sodium thiosulfate at about a 0.3% level and ethylenediaminetetraacetic acid at about 0.05%.

It goes without saying that the precise ophthalmic carrier must be selected to provide pharmaceutical elegance, to provide eye comfort and to allow for effective topical administration. Formulation of such is well within the skill of the ordinary artisan who prepares ophthalmic carrier compositions.

The compounds used as the anti-inflammatories of this invention have features which enhance the aqueous solubility of the anti-inflammatory drug while retaining sufficient lipid solubility to promote intracellular and in particular intraocular penetration. They also will maintain the pharmacophore necessary to exhibit anti-inflammatory activity. The compounds thus take into account both solubility for sufficient ocular penetration and anti-inflammatory activity, and balance these in unique compounds duly suited for the unique penetration and distribution processes for drugs in the eye.

The following examples serve to further illustrate but not limit the compounds, compositions and method of the present invention. A rabbit cornea model was used in the tests shown in the examples because, as those of ordinary skill in the art know, rabbit cornea testing has been mostly correlated with test results for the human eye, R. D. Schoenwald et al Biopharm. Drug Dispos., 3, 231 (1982).

EXAMPLE I

Excised rabbit corneas were carefully mounted between two halves of a plastic cylinder. Various concentrations of Ibuprofen as a comparative model:

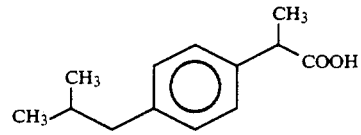

or the compound of the present invention wherein R equals H and Z equals oxygen, m equals O, and n equals 2, were placed on the epithelial side initially and drug appearing on the endothelial side was measured over time.

The slope from the quantity of drug crossing the excised cornea over time was used to calculate the corneal permeability coefficient (cm/sec):

TABLE I

| Initial Cell Conc. (mcg/mL) | Permeability Coefficient ($\times 10^6$ cm/sec) | |
|---|---|---|
| | Ibuprofen | Invention |
| 500 | 21.6 | — |
| 250 | 23.9 | 6.42 |
| 150 | 21.2 | 6.65 |
| 60 | 22.8 | 6.53 |
| | mean = 22.4 | mean = 6.53 | pH = 7.6, temp. = 37, 95% $O_2$ 5% $CO_2$

The solubilities of the two were compared and found to be as follows:

Ibuprofen: 75 mcg/mL (in dist. water, pH=5.5)
(Invention): 5000 mcg/mL (in dist. water, pH=5.0)

When the maximum penetration rate (MPR) is calculated: MPR=(SOL) (Per. Coeff.), Ibuprofen equals 1.68 mg/cm$^2$/sec and the invention is 32.7 mg/cm$^2$/sec. Thus, the invention has a 19.5 fold greater corneal penetration rate.

Corneal anti-inflammatory activity was compared. The Leibowitz anti-inflammatory model was used, H. M. Leibowitz and A. Kupferman, "Anti-inflammatory effectiveness in cornea of topically administered prednisolone," *Invest. Ophthalmol.*, 13, 757 (1974) and H. M. Leibowitz and A. Kupferman, "Bioavailability and therapeutic effectiveness of topically administered corticosteroids," *Trans. Am. Acad. Ophthalmol. Otolaryngol.*, 79, 78 (1975). This method consists of first injecting tritiated thymidine intraenously into white rabbits. In approximately 2 days, the radioactive, thymidine is incorporated into polymorphonuclear leucocytes (PMN) which upon injection of clover oil into the stroma of the cornea will migrate to the site of injection. Topical treatment of non-steroidal anti-inflammatory drugs, if effective, will suppress the migration of polymorphonuclear cells to the injection site. The reduction of radioactivity in the cornea becomes a measure of drug effectiveness to suppress the inflammation process. The results are summarized below as a percent reduction of radioactivity occurring from no drug treatment.

TABLE II

| Drug Treatment* | DPM** | % Decrease (compared to control) |
|---|---|---|
| Invention 1% Solution | 6720 (sd = 3368) | 19 |
| Prednisolone Acetate 1% Suspension | 4288 (sd = 2846) | 48 |
| No Treatment | 8255 (sd = 5956) | 0 |

*Drug treatment started at the time of clove oil injection (N = 6/treatment group); all treatment groups received 8-9 doses/day of invention.
**Disintegrations per minute Prednisolone acetate was used as a comparative, highly effective steroidal anti-inflammatory, which like many of the other effective ones is known to produce certain undesirable side effects.

The initial results for the topical instillation of 1% of the invention show a 19% decrease in corneal inflammation following clove oil chemotaxis. These results for the invention are significantly less potent than the results observed for 1% prednisolone acetate suspension. This is not surprising in light of the superior potency of steroids, particularly prednisolone acetate, and the generally lower potency of non-steroidal anti-inflammatory drugs. The values obtained for 1% prednisolone acetate agree with published results by Leibowitz. Ibuprofen itself is reported to be effective for post-operative corneal inflammation in patients taking 1200 Gm/day, but no reports are published to indicate its topical efficacy on corneal inflammation. The superior permeability characteristics of the compound of the present invention over Ibuprofen indicates much higher effective activity without systemic side effects.

EXAMPLE II

Synthesis of 2-[4-(3-hydroxypropoxy)phenyl]propionic acid

Ethyl 2-[4-hydroxyphenyl]propionate [20 mmole] was combined with 3-chloropropanol [22 mmole] and potassium carbonate [24 mmole] in acetone [100 ml], then refluxed for 18 hours. After removal of the acetone under reduced pressure, the reaction mixture was extracted with 1N sodium hydroxide solution to remove acidic components. These were chromatographed on silica gel/toluene to isolate the product, 2-[4-(3-hydroxypropoxy)phenyl]propionic acid, as an amorphous solid. Mass spectral, proton nuclear magnetic resonance, and elemental analysis data are consistent with the assigned structure. Additional product was obtained by basic hydrolysis of the neutral fraction, followed by silica gel/toluene chromatography.

EXAMPLE III

Synthesis of 2-[4-(2-hydroxypropoxy)phenyl]propionic acid

Ethyl 2-[4-hydroxyphenyl]propionate [50 mmole] was combined allyl bromide [60 mmole] and potassium carbonate [60 mmole] in acetone [250 ml], then refluxed for 18 hours. Reaction of the product, ethyl 2-[4-allyloxyphenyl]propionate [50 mmole], with 3-chloroperoxybenzoic acid [60 mmole] in methylene chloride [100 ml] under reflux [24 hrs] formed the corresponding epoxide which was treated with hydrogen and 10% palladium on charcoal in methanol to yield ethyl 2-[4-(2-hydroxypropoxy)phenyl]propionate. Hydrolysis of the ethyl ester with potassium hydroxide followed by neutralization of the reaction mixture with dilute sulfuric acid yielded 2-[4-(2-hydroxypropoxy)phenyl]propionic acid, as a white amorphous solid after silica gel/toluene chromatography. Mass spectral, proton nuclear magnetic resonance, and elemental analysis data are consistent with the assigned structure.

EXAMPLE IV

Efficacy data for II and III

Sodium arachidonate (Sigma Chemical Co., St. Louis, Mo.) 0.5% was prepared in a phosphate-buffered (pH 7) isotonic vehicle within one hour of use. The test compound, {2-[4-(2-hydroxypropoxy)phenyl]propionic acid}, was dissolved in the same vehicle at 0.5, 1, 2 and 4% w/v and stored at room temperature until needed. Each rabbit received 20 uL of drug solution in one eye and an equal volume of vehicle in the other eye. In ten minutes 20 uL of arachidonate solution was instilled in both eyes. All eyes were graded for the following signs of inflammation: lid closure (Table III) (every 15 min. through 1 hour), mucous discharge (Table IV) (every 15 min. through 1 hour), chemosis (at the end of 1 hour) and hyperemia (at the end of one hour) (Table V). The method, as well as the grading technique, was followed according to procedures of M. B. Abelson, et al. (Jr. of Ocular Pharmacology, 3, 63-74, 1987). The same six rabbits were used for each % drug evaluation; each rabbit was allowed to recover for at least one week before applying test solution again. Another test agent, {2-[4-(3-hydroxypropoxy)phenyl]propionic acid} and referred to as the compound of Example II was tested at 1%; however, 50 uL was administered to the rabbit eye.

TABLE III

| Results | | LID CLOSURE | | | |
|---|---|---|---|---|---|
| Minutes | | 15 | 30 | 45 | 60 |
| Comp. of Ex. II | 1.0% | 2.00 | 1.78 | 2.22 | 1.78* |
| Vehicle | | 2.22 | 2.33 | 2.78 | 2.44 |
| Comp. of Ex. III | 0.5% | 2.33* | 2.33* | 2.50** | 2.33** |
| Vehicle | | 3.00 | 2.83 | 2.83 | 2.83 |
| Comp. of Ex. III | 1.0% | 2.00* | 2.17 | 1.50 | 1.67 |

TABLE III-continued

| Results | | LID CLOSURE | | | |
|---|---|---|---|---|---|
| Minutes | | 15 | 30 | 45 | 60 |
| Vehicle | | 2.67 | 2.50 | 1.83 | 2.00 |
| Comp. of Ex. III | 2.0% | 1.67* | 1.50* | 1.50* | 1.50** |
| Vehicle | | 2.50 | 2.50 | 2.17 | 2.17 |
| Comp. of Ex. III | 4.0% | 1.17* | 1.33** | 1.17* | 0.83* |
| Vehicle | | 2.50 | 2.00 | 2.17 | 2.00 |

TABLE IV

| | | MUCOUS DISCHARGE | | | |
|---|---|---|---|---|---|
| Minutes | | 15 | 30 | 45 | 60 |
| Comp. of Ex. II | 1.0% | 1.11 | 1.22 | 1.33 | 1.33 |
| Vehicle | | 1.11 | 1.11 | 1.11 | 1.33 |
| Comp. of Ex. III | 0.5% | 0.67 | 1.33** | 1.50 | 1.50 |
| Vehicle | | 0.50 | 1.83 | 1.83 | 1.83 |
| Comp. of Ex. III | 1.0% | 1.17 | 1.33 | 1.50 | 1.33 |
| Vehicle | | 1.00 | 1.17 | 1.00 | 1.17 |
| Comp. of Ex. III | 2.0% | 0.67 | 0.50 | 0.33 | 0.67 |
| Vehicle | | 0.17 | 0.50 | 0.50 | 0.50 |
| Comp. of Ex. III | 4.0% | 0.50* | 0.83 | 1.00 | 0.83 |
| Vehicle | | 0.83 | 1.00 | 1.17 | 1.17 |

TABLE V

| Minutes | | CHEMOSIS 60 | CONJUNCTIVAL HYPEREMIA 60 |
|---|---|---|---|
| Comp. of Ex. II | 1.0% | 2.44 | 2.22 |
| Vehicle | | 2.44 | 2.22 |
| Comp. of Ex. III | 0.5% | 1.33* | 1.50* |
| Vehicle | | 2.00 | 2.00 |
| Comp. of Ex. III | 1.0% | 2.00 | 1.50 |
| Vehicle | | 2.00 | 1.67 |
| Comp. of Ex. III | 2.0% | 1.33** | 1.50 |
| Vehicle | | 1.83 | 1.83 |
| Comp. of Ex. III | 4.0% | 1.00** | 1.17 |
| Vehicle | | 1.50 | 1.17 |

*Statistically significant at p < 0.05;
**Statistically significant at p < 0.1; all other values n.s.

The vehicle has no effect in inhibiting the inflammatory reaction initiated by sodium arachadonate. However, the drug solution of Example III is statistically significant at various time intervals for each test concentration of the example of Compound III and for various inflammatory reactions produced in the rabbit eye (i.e., lower in scoring than the vehicle control). The compound of Example II was also active, but only for the lid closure response and only at 60 minutes after dosing. The compound of Example III is considered more active according to the results of this testing procedure.

For each of Tables III-V, the lower the number the more effective the drug.

What is claimed is:

1. The compound of the formula:

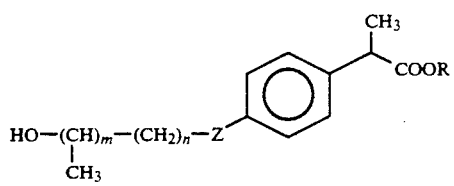

wherein R=H, $C_1$ to $C_6$ straight and branched chain alkyls with or without an additional hydroxyl, 6- or 1-[2-deoxy-a-D-arabino-hexopyranoside], and N,N-di(2-hydroxyethyl)-2-hydroxyacetamide or other hydrophilic glycolamides; Z is oxygen; n=1 to 4; m=0 or 1, and ophthalmically acceptable salt forms thereof.

2. A compound of claim 1 wherein R equals hydrogen.

3. A compound of claim 1 wherein m and n are one, R equals hydrogen and Z equals oxygen.

4. A method of effectively and topically treating both external and internal inflammations of the eye so as to reduce unwanted systemic side effects, with nonsteroidal drugs capable of eye penetration, said method comprising:

administering to an affected eye an external and internal inflammation reducing effective amount of a compound of the formula:

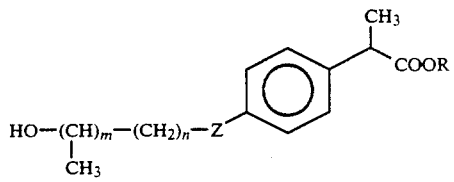

wherein R=H, $C_1$ to $C_6$ straight and branched chain alkyls with or without an additional hydroxyl, 6- or 1-[2-deoxy-a-D-arabino-hexopyranoside], and N,N-di(2-hydroxyethyl)-2-hydroxyacetamide or other hydrophilic glycolamindes; Z=oxygen or methylene; n=1 to 4; m=0 or 1, and opthalmically acceptable salt forms thereof which penetrates the eye.

5. A method of claim 4 wherein m and n are one; R equals hydrogen and Z equals oxygen.

6. The method of claim 5 wherein R equals hydrogen.

7. The method of claim 5 wherein Z equals oxygen.

8. The method of claim 5 wherein the amount of said compound is from about 0.025% by weight to about 5.0% by weight.

9. The method of claim 5 wherein the amount of said compound is from about 0.5% by weight to about 3.0% by weight.

10. A nonsteroidal pharmaceutical composition for topically treating external and internal inflammation of the eye comprising an external and internal inflammation reducing effective amount of a compound of the formula:

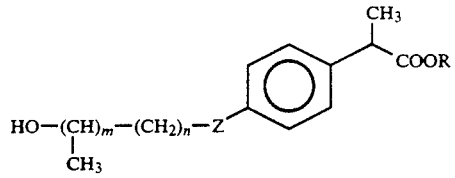

wherein R=H, $C_1$ to $C_6$ straight and branched chain alkyls with or without an additional hydroxyl, 6- or 1-[2-deoxy-a-D-arabino-hexopyranoside], and N,N-di(2-hydroxyethyl)-2-hydroxyacetamide or other hydrophilic glycolamides; Z=oxygen or methylene; n=1 to 4; m=0 or 1, and ophthalmically acceptable salt forms thereof and an ophthalmically effective carrier therefore.

11. A composition of claim 10 wherein m and n are one, R equals hydrogen and Z equals oxygen.

12. The composition of claim 10 wherein the amount of said compound is from about 0.025% by weight to about 5.0% by weight.

13. The composition of claim 12 wherein the amount of said compound is from about 0.5% by weight to about 3.0% by weight.

14. The composition of claim 11 wherein said composition is an eye drop solution.

15. The composition of claim 11 wherein said composition is an ointment.

16. The composition of claim 11 wherein said composition is an ophthalmic gel.

17. The composition of claim 11 wherein said composition is a nonaqueous suspension.

* * * * *